United States Patent [19]

Kiyobe et al.

[11] Patent Number: 4,674,325
[45] Date of Patent: Jun. 23, 1987

[54] MICROWAVE MOISTURE SENSOR

[75] Inventors: Seiichiro Kiyobe; Tokio Hirano, both of Tokyo, Japan

[73] Assignee: Yokogawa Hokushin Electric Corporation, Tokyo, Japan

[21] Appl. No.: 807,126

[22] Filed: Dec. 11, 1985

Related U.S. Application Data

[63] Continuation of Ser. No. 599,787, Apr. 13, 1984, abandoned.

[30] Foreign Application Priority Data

Dec. 23, 1983 [JP] Japan ............................ 58-243564

[51] Int. Cl.⁴ .......................................... G01R 27/04
[52] U.S. Cl. ............................. 73/73; 73/159; 324/58.5 A
[58] Field of Search ............... 73/73, 159; 250/300; 374/126; 324/81.5 A, 81.5 B; 370/7

[56] References Cited

U.S. PATENT DOCUMENTS

| | | | |
|---|---|---|---|
| 3,034,046 | 5/1962 | Sasaki | 324/58.5 A |
| 3,392,282 | 7/1968 | Astheimer | 374/126 |
| 3,619,511 | 11/1971 | Ishikawa | 370/7 |
| 3,782,192 | 1/1974 | Sandblom | 73/159 |
| 4,301,365 | 11/1981 | Basin | 250/308 |
| 4,324,136 | 4/1982 | Ashford | 73/159 |
| 4,424,443 | 1/1984 | Reuland | 250/308 |
| 4,484,133 | 11/1984 | Riggin | 324/58.5 A |
| 4,485,284 | 11/1984 | Pakulis | 73/73 |

FOREIGN PATENT DOCUMENTS

| | | | |
|---|---|---|---|
| 859602 | 1/1961 | United Kingdom | 370/7 |
| 543290 | 10/1975 | U.S.S.R. | 73/73 |

OTHER PUBLICATIONS

Microelectronics; by Millman; copyright 1979, pp. 596–600 and pp. 183 and 184.
Electron Tube Circuits; Seely; copyright 1950; pp. 483, 484, 485.

Primary Examiner—Charles Frankfort
Assistant Examiner—Denis E. Corr
Attorney, Agent, or Firm—Moonray Kojima

[57] ABSTRACT

A microwave moisture sensor operates on the principle that an emitted microwave is attenuated in rotary resonance with water molecules. The microwave moisture sensor includes measurement and reference signal systems sharing a microwave oscillator, a detector and other components, means for calculating the ratio of the signals from the respective systems, and an AGC circuit means for keeping the reference signal from the reference signal system at a predetermined level, so that drifts of the microwave oscillator, detector and other components will be cancelled and thus increased measuring accuracy will result. Furthermore, the microwave moisture sensor measure the basis weight and temperature of a material being measured, and processes the measured values according to predetermined moisture percentages free from adverse influences of the basis weight and temperature and thus increase the degree of measurement accuracy.

3 Claims, 10 Drawing Figures

MICROWAVE MOISTURE SENSOR

This is a continuation of application Ser. No. 599,787 filed Apr. 13, 1984 and now abandoned.

BACKGROUND OF THE INVENTION

1. Field of Invention

This invention relates to a microwave moisture sensor which operates on the principle that an emitted microwave is attenuated in rotary resonance with water molecules, and more particularly to a microwave moisture sensor comprising a microwave transmitter and a microwave receiver spaced a distance from each other in confronting relation for producing a signal, indicative of the water content in a sheet of material to be measured, which travels between the microwave transmitter and receiver.

2. Description of Prior Art

Microwave moisture sensors are known in the art. One example of such a prior sensor is depicted in FIG. 1 and comprises a detector head 30 having metal casings 1,2 housing a microwave transmitter and a microwave receiver. The detector head 30 is mounted on a centrally open frame 31, as shown in FIG. 2, for reciprocally scanning a sheet of paper 23 in a transverse direction thereof, across a zone between limits L1 and L2, to thereby measure the moisture or water content in sheet of paper 23, which travels in the direction of the arrow A, through frame 31. Casing 1 accommodates the microwave transmitter and receiver, generally designated by 6 and 10, respectively. Microwave transmitter 6 includes a microwave oscillator 3, an isolator 4, and a microwave transmitting horn antenna 5. Microwave receiver 10 includes a microwave receiving horn antenna 7, a detector (e.g. Schottky diode) 8, and a signal amplifier 9 which amplifies a detected signal and supplies the amplified signal to a signal processor (not shown). The signal processor is supplied with the signal from detector head 8 and a preset signal, representative of the basis weight of paper 23, and processes the supplied signals based on a predetermined calibration curve. Detector 8 comprises a heterodyne detector energized by a local oscillator (not shown) which generates a signal having a frequency different from that of the signal produced by microwave oscillator 3. Casing 2 has a microwave receiving horn antenna 11 which cooperates with antenna 5 and together can be considered to constitute a transmitting and receiving pair. Also in casing 2 is a microwave transmitting horn antenna 12 which cooperates with antenna 7 and together can be considered to constitute another transmitting and receiving pair. Antenna 12 is connected to antenna 11 by a coaxial cable 13 for transmitting the microwave that has been received by antenna 11. Casings 1,2 have microwave transmitting and receiving ports closed by thin films 18,19, 20,21, which films may be of such a material as polyethylene terephthalate.

For moisture measurement, the microwave moisture sensor moves detector head 30 to scan the sheet of paper 23, transversely across the zone L1-L2 (see FIG. 2). At this time, a microwave emitted from transmitter 6 to paper 23 travels from antenna 5 through space 14 and film 18 to paper 23, then through film 20 and space 16 to antenna 11, then to coaxial cable 13, then to antenna 12, then through space 17 and film 21 to paper 23 and then through film 19 and space 15 to antenna 7, Then, the microwave is detected by detector 8. The signal processor (not shown) is responsive to the detected signal, as amplified by amplifier 9, and to the preset signal, indicative of the basis weight of the paper 23, for processing these signals based on the calibration curve, to thereby generate a signal representative of the water content or moisture in paper 23.

The prior microwave moisture sensor just described is disadvantageous in that its measurement accuracy is low since the moisture dependent signal (input signal) fed to the signal processor contains drifts of the microwave oscillator, the detector and other devices.

Another problem with the conventional microwave moisture sensor is that with the basis weight signal applied to the signal processor being preset, the measurement accuracy is lowered when the basis weight of the paper is changed during measurement. It should be noted that the basis weight of paper of one brand or manufacturer may vary in the actual paper making plant.

In addition, the measurement accuracy is also lowered when the paper is subjected to temperature variations because the degree to which the paper absorbs microwaves, varies with the temperature.

SUMMARY OF THE INVENTION

Accordingly, an object of the invention is to improve the prior art and to overcome the aforementioned and other deficiencies and disadvantages of the prior art.

Another object is to provide a microwave moisture sensor capable of cancelling out adverse affects of drifts from the microwave oscillator, the detector and other components, to thereby increase measurement accuracy.

A further object is to provide a microwave moisture sensor which is capable of compensating for variations in the basis weight and the temperature of an object to be measured, to thereby increase measement accuracy.

The foregoing and othe objects are attained by the present invention which encompasses a microwave moisture sensor, wherein means are provided for switching a microwave generated by a microwave oscillator between measurement and reference systems, with a switch, detecting the microwaves propagated through the respective systems with the same detector, delivering detected signals to a signal processor through sample-and-hold circuits, and determining moisture percentage by using a signal indicative of the ratio between measurement and reference signals from the measurement and reference systems. An automatic gain control (AGC) circuit may be disposed preceding the sample-and-hold circuits for keeping the reference signal at a prescribed level. Means are provided for measuring the basis weight and temperature of the material being measured, and effecting basis weight compensation and temperature compensation, based on predetermined temperature compensation of moisture percentage parameters, and predetermined gauge reading versus basis weight characteristics of the moisture percentage parameters.

DETAILED DESCRIPTION OF PREFERRED EMBODIMENTS

Figure 1:
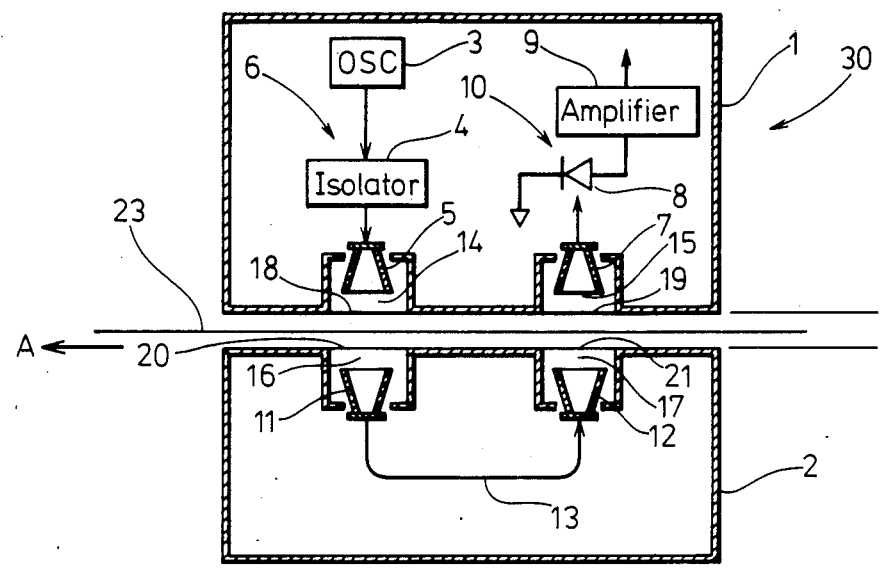
FIG. 1 is a schematic view depicting a conventional microwave moisture sensor.
Figure 3:
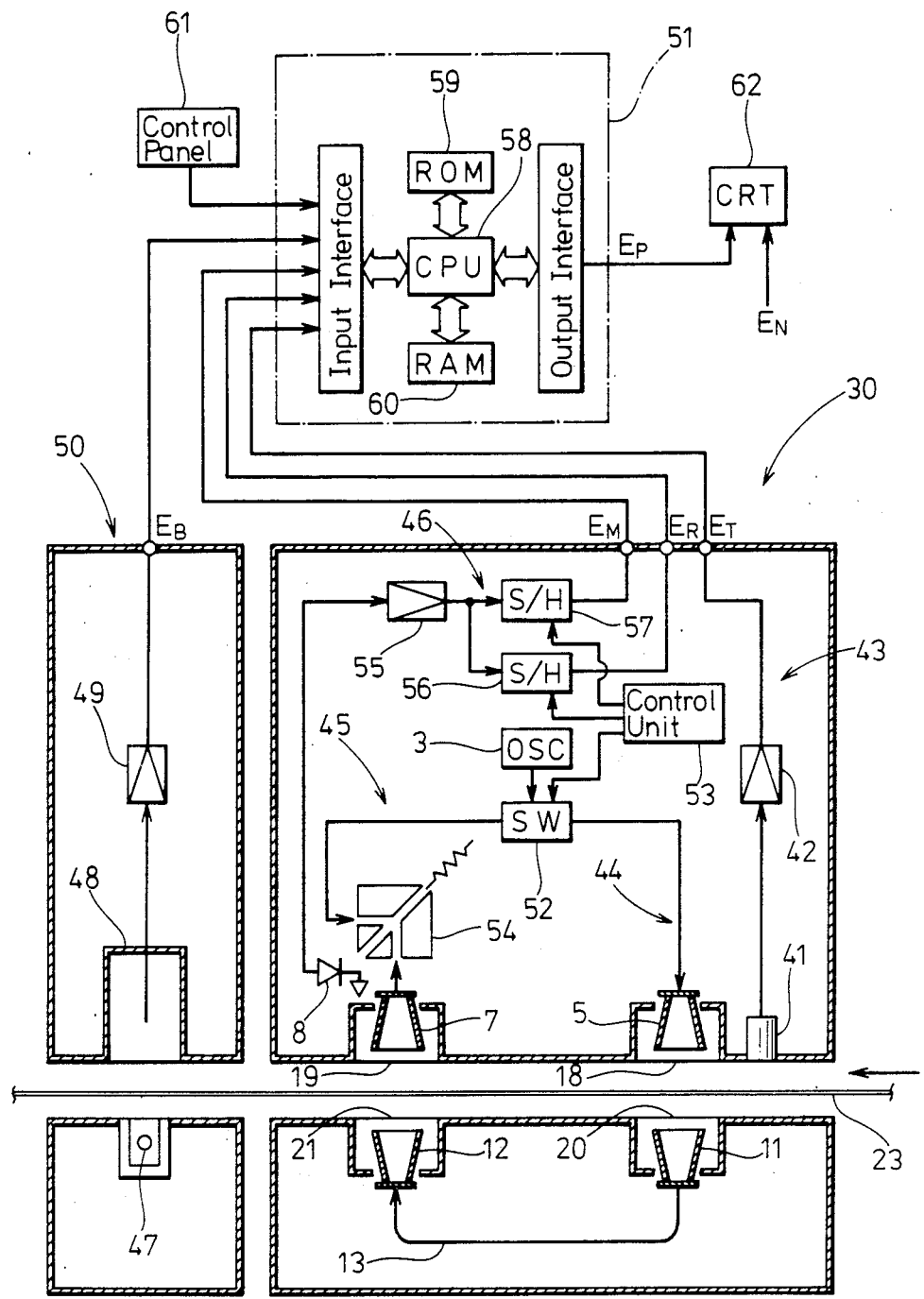
FIG. 3 is a schematic view, partly in block diagram, depicting an illustrative embodiment of the invention.

FIG. 3 shows a microwave moisture sensor according to the illustrative embodiment of the invention. Similar or corresponding parts in FIG. 3 are denoted by similar or corresponding reference characters in FIG. 1, and will not be described hereat in detail for sake of clarity of description.

Detector head 30, in the microwave moisture sensor, comprises a temperature measuring unit 43, which supplies signal $E_T$; a moisture detector 46, which supplies measurement signal $E_M$ and reference signal $E_R$; measurement system 44; reference system 45; and basis weight detector 50, which supplies signal $E_B$.

Temperature measuring unit 43 amplifies signal detected by a radiation temperature detector 41, with an amplifier 42, and supplies a signal $E_T$. Moisture detector 46 supplies signal $E_M$ and reference signal $E_R$ selectively by use of switch 52, controlled by control unit 53, in a manner to be described. Switch 52 and control unit 53 switch a microwave, produced by microwave oscillator 3, between measurement system 44 which comprises a propagation path comprising, for example, microwave transmitting and receiving antennas 5,11,12,7; and reference system 45 which comprises a propagation path comprising for example, detector 8 and magic "T" 54. The reference system 45 may be considered to have a propagation path which excludes the measurement system.

Basis weight detector 50 comprises a radiation heat source 47 and an ionization chamber 48 which are disposed in confronting relation on opposite sides of the sheet of paper 23, and an amplifier 49 for amplifying a signal indicative of a beta ray transmitted through paper 23 and detected by ionization chamber 48. Temperature measuring unit 43, moisture detector 46, and basis weight detector 50 may be both accommodated in casings which are mounted on a centrally open frame for scanning paper 23 transversely across a prescribed zone on paper 23 and operated cooperatively to apply signals to a signal processor 51.

Measurement system 44 comprises and is constructed to propagate a microwave from a microwave transmitting antenna 5 through film 18, paper 23 and film 20 to a microwave/receiving antenna 11 and then through coaxial cable 13 to a microwave transmitting antenna 12 and then through film 21, paper 23 and film 19 to a microwave receiving antenna 7 and then to a magic "T" 54 and then to a detector 8. The magic "T" is a means for guiding, without interference, microwaves which are entered from two microwave inlet ports, to a single microwave outlet port.

Reference system 45 comprises and is constructed to propagate a microwave directly ( although in practice the microwave is transmitted through an attenuator) through magic "T" 54 to detector 8. The signal, as detected by detector 8, is amplified by an amplifier 55. Thereafter reference signal $E_R$ from reference system 45 is fed to a sample-and-hold circuit 56 and measurement signal $E_M$ from measurement system 44 is fed to sample-and-hold circuit 57, all via amplifier 55, and under the control of control unit 53. The timing of the operation of the gates of sample-and-hold circuits 56, and 57, is controlled by control unit 53, in synchronism with switching operation of switch 52.

Moisture detector 46 comprises amplifier 55, sample-and-hold circuit 56,57, oscillator 3, switch 52 and control unit 53, which operate in the manner described.

Signal processor 51 comprises a computer having a central processing unit (CPU) 58, a read only memory (ROM) 59, a random access memory (RAM) 60 and input and output interfaces (not numbered) for processing signals from detector head 30, a signal from a control panel 61, and other signals, thereby to generate a moisture content signal $E_P$ which may be an ordinate axis signal, which signal is then supplied to a display unit 62, such as a cathode ray tube (CRT). A signal $E_N$ indicative of the measuring points which are located transversely across the paper 23, are applied as an abscissa axis signal to CRT 62.

Figure 4:
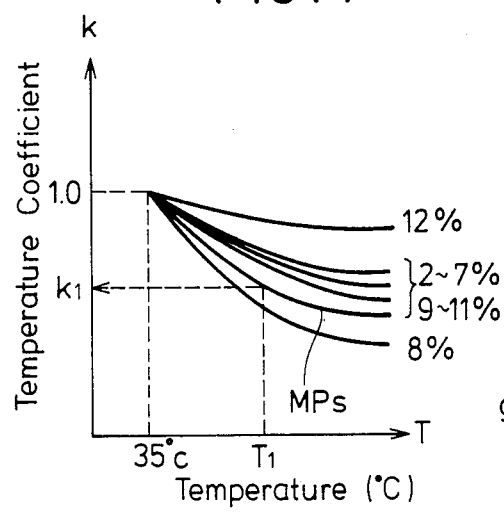
FIG. 4 is a graph depicting characteristic curves of temperature compensation of moisture percentage parameters.

ROM 59 stores data on temperature compensation characteristics of water percentage parameters, which are determined for a paper brand cut to prescribed dimensions (see FIG. 4 where the ordinate indicates compensation coefficient and the abscissa indicates temperature ); data on moisture content versus basis weight characteristics of water percentage parameters (See FIG. 5 where the ordinate indicates water content and the abscissa indicates basis weight); and a program for sampling signals which are supplied by the respective detectors at prescribed sampling times, for determining water percentage using the temperature compensation characteristics and the moisture content versus basis weight characteristics, and for generating a moisture percentage signal $E_P$.

Figure 6:
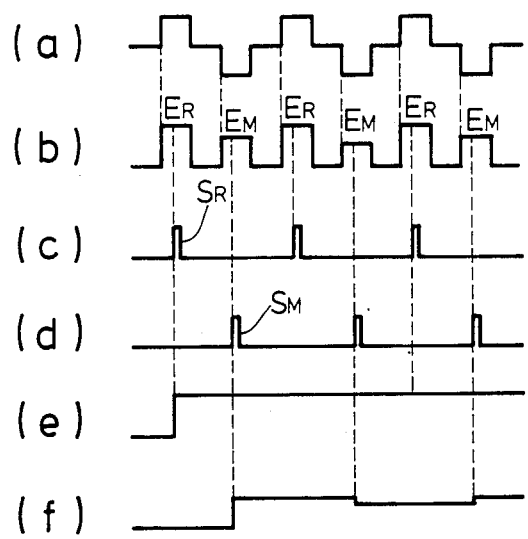
FIG. 6 is a diagram depicting signal waveforms illustrative of operation of the embodiment.

In operation, switch 52 in moisture detector 46 operates under the control of a control signal, such as shown in FIG. 6, line (a), supplied by control unit 53, to allow the output microwave from oscillator 3 to be switched alternately to antenna 5 and magic "T" 54. The signal detected by detector 8 therefore becomes a time series signal comprising, as shown in FIG. 6, line (b), signal $E_R$ from reference system 45, and signal $E_M$ from measurement system 44. The gates of sample-and-hold circuits 56,57 are controlled by signals $S_R$, $R_M$ such as shown in FIG. 6, line (c) and line (d), synchronously with the switching operation of switch 55, such that the gate of sample-and-hold circuit 56 will open when the microwave goes through reference system 45 and the gate of sample-and-hold circuit 57 will open when the microwave goes through measurement system 44. Output signals $E_R$, $E_M$ from sample-and-hold circuits 56,57 are as depicted in FIG. 6, lines (e) and (f), respectively, and supplied to processor 51. The temperature measuring unit 43 supplies to processor 51 a signal $E_T$ representing the surface temperature T of paper 23, while the basis weight detector 50 supplies a signal $E_B$ to processor 51, which represents basis weight BW of paper 23.

Figure 2:
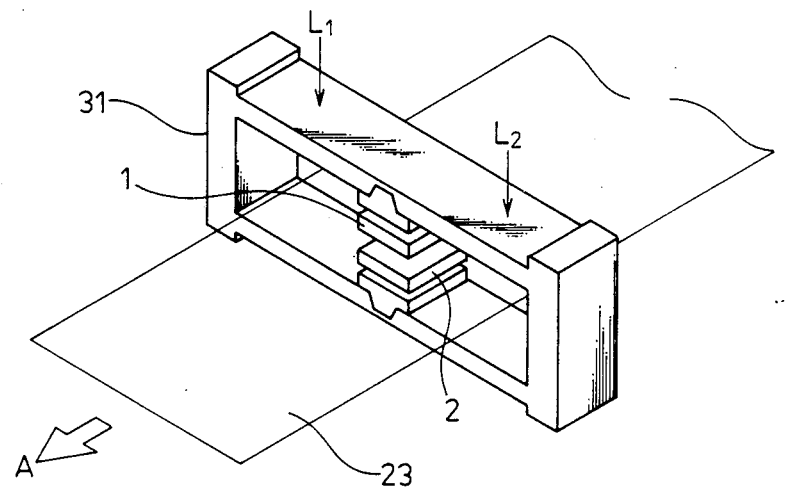
FIG. 2 is a perspective view depicting a centrally open frame on which a detector head of a microwave moisture sensor is mounted.

During a first forward scanning stroke, from L1 to L2, for example in FIG. 2, of detector head 30, signal processor 51 samples the input signal from detectors N (N being a natural number) times with N sampling signals which equally divide one scanning time and then effects the below arithmetic operations (1) through (5). Since detector head 30 scans paper 23 at a constant speed, signals obtained by the above sampling operation, can be regarded as measured values at N measuring points (hereinafter referred to as measuring points $N_1, N_2 \ldots N_n$) defined transversely on paper 23.

(1) The ratio between signals $E_M$, $E_R$ is calculated. (This advantageously cancels drifts of oscillator 3, detector 8, and other components). The ratio corresponds to a measured water content $G_1$ (MW).

(2) Temperature signal $E_T$ is linearize, and a radiation coefficient is corrected and the surface temperature $T_1$ of paper 23 is determined.

(3) A compensation coefficient $k_1$ is determined (see FIG. 4) using a characteristic curve wherein a preset water percentage $MP_s$ in the temperature compensation characteristics is employed as a parameter, or a characteristic curve closest to the above characteristic curve, and the surface temperature $T_1$, and then temperature compensation of $k_1 \times g_1$ (MW) is calculated.

Figure 5:
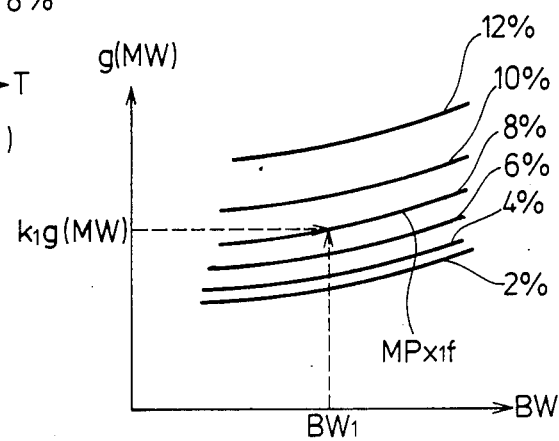
FIG. 5 is a graph depicting characteristic curves of moisture content versus basis weight of moisture percentage parameters

(4) Temperature compensated moisture content $k_1 \times g_1$ (MW) and basis weight BW (which can be determined from basis weight signal $E_B$), and gauge reading versus basis weight characteristics, are used to determine a moisture percentage $MP_{x1f}$ (see FIG. 5).

(5) Moisture percentage $MP_{x1f}$ is stored in RAM 60 and delivered to CRT 62.

By performing the foregoing arithmetic operations (1) through (5), N times, moisture percentages $MP_{x1f}$, $MP_{x2f}, \ldots MP_{x(n-1)f}$, $MP_{xnf}$ can be determined respectively for the measuring points $N_1, N_2, \ldots, N_{n-1}, N_n$ in the first forward scanning stroke. Then, detector head 30 enters a first return or rearward scanning stroke by moving from L2 to L1. The signal processor 51 effects above arithmetic operations (1) through (5) in such a rearward scanning stroke.

In the first return scanning stroke and subsequent scanning strokes (second forward and return scanning strokes, for example), the arithmetic operation (3) carries out temperature compensation by determining a compensation coefficient with a temperature compensation characteristic curve in which the previous moisture percentage is used as a parameter. More specifically, since input signals are applied to the signal processor 51 in the first return scanning stroke from measuring points $N_n, N_{n-1}, \ldots, N_2, N_1$ in the order named, the arithmetic operation (3) performs temperature compensation while determining temperature compensation coefficients by successively using characteristic curves in which the moisture percentages $MP_{xnf}, MP_{x(n-1)f}, \ldots, MP_{x2f}, MP_{x1f}$, or moisture percentages closest thereto, are employed as parameters. Accordingly, the moisture percentages determined in the first return scanning stroke are defined as $MP_{xnb}, MP_{x(n-1)b}, \ldots, MP_{x2b}, MP_{x1b}$ corresponding respectively to the measuring points.

Signal processor 51 then continues to effect the above arithmetic operations for subsequent scanning strokes of detector head 30 and successively delivers to CRT 62 signals $E_P$ indicative of moisture percentages which are temperature compensated and basis weight compensated at the measuring points across the paper width. Thus, the operator can see an accurate distribution or profile of moisture percentages transversely across the paper.

Figure 7:
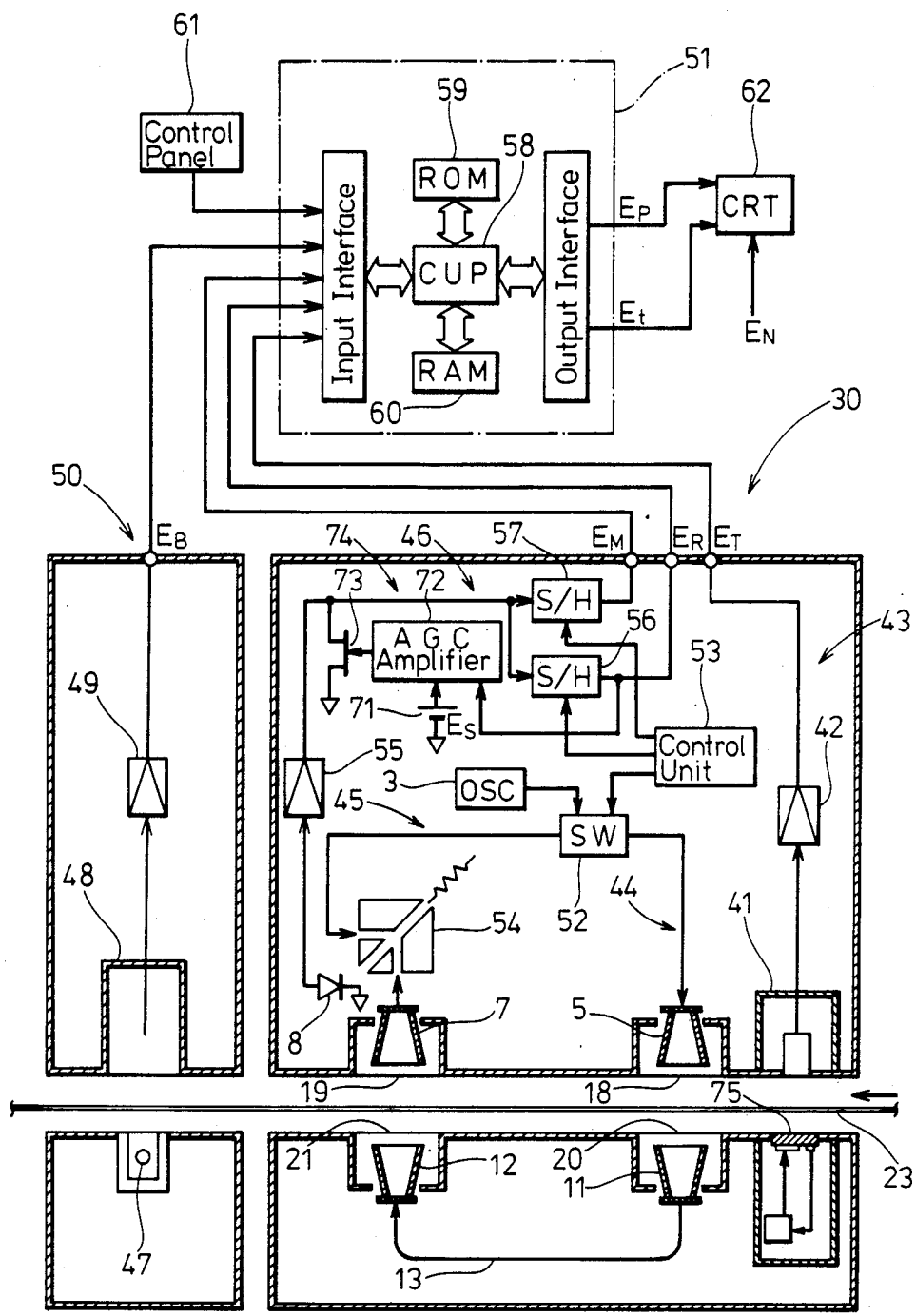
FIG. 7 is a schematic view, partly in block diagram, depicting another illustrative embodiment of the invention.

FIG. 7 depicts another illustrative embodiment of the invention. Similar or corresponding parts in FIG. 7 are denoted by similar or corresponding reference characters in FIGS. 1 and 3, and are not described hereat for sake of simplification of description. In FIG. 7, an AGC (automatic gain control) circuit 74 is used in the embodiment, and comprises an AGC amplifier 72 for adding and integrating a signal $E_R$ and an output signal $E_S$ supplied from a constant voltage source 71, and a field effect transistor 73 connected between an output terminal of amplifier 55 and a point of reference potential. The transistor 73 is controlled by an output signal from AGC amplifier 72.

A body 75 (see FIG. 8) having a constant radiation coefficient is used for calibrating temperature measuring unit 43. ROM 59 stores a program for delivering a signal $E_t$ representative of the difference between a signal $E_T$ and a predetermined temperature as an ordinate axis signal to a display 62. The microwave sensor shown in FIG. 7 is designed particularly for measuring the moisture content of paper delivered from a calender roll in a paper making plant.

Figure 8:
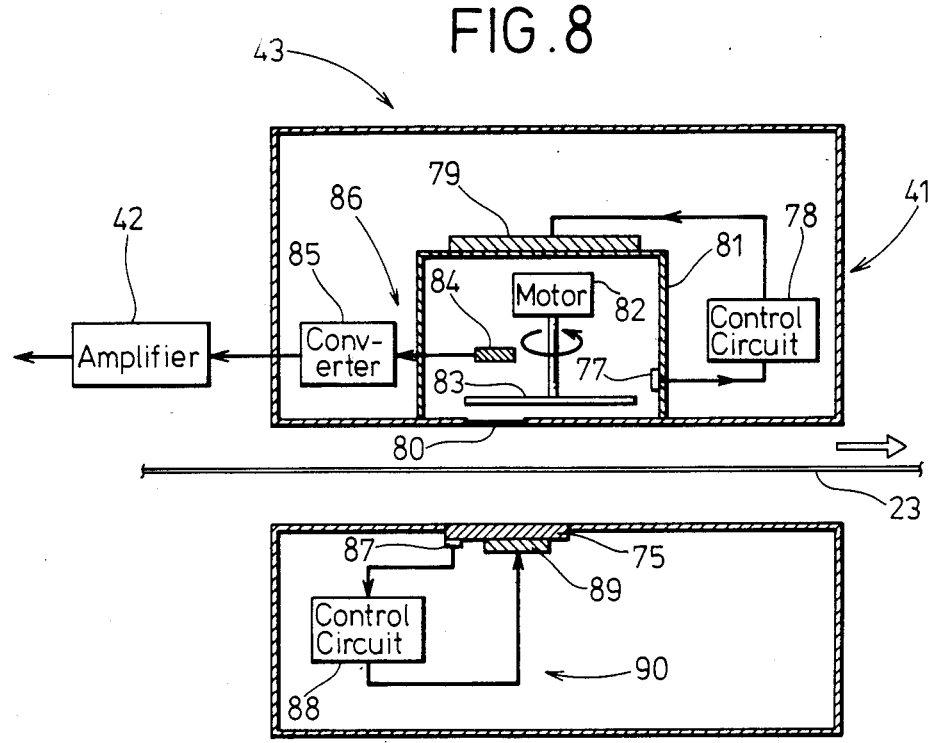
FIG. 8 is a schematic view depicting a temperature measuring unit used in the embodiment of FIG. 7.
Figure 9:
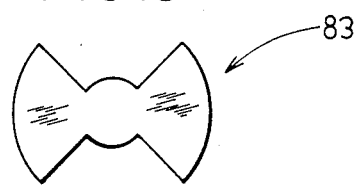
FIG. 9 is a plan view depicting a rotary sector unit used in the temperature measuring unit shown in FIG. 8.

As illustrated in FIG. 8, temperature measuring unit 43 includes a temperature control system comprising a temperature sensor 77, a control circuit 78, and a heater 79 for keeping the interior of temperature measuring unit 43 at a substantially constant temperature, such as 50° C., for example. Temperature measuring unit 43 also has a constant temperature chamber 81 for introducing through a window 80 radiation from paper 23, kept at a temperature within the range of from 40° C. to 130° C. and moving in the direction of the arrow (not numbered). A rotary sector 83 (see FIGS. 8 and 9) is disposed in constant temperature chamber 81 and is rotatable by a motor 82 at a substantially constant speed. The shape of rotary sector 83 may be as shown in FIG. 9.

A temperature detecting system 86 comprising an infrared sensor 84 disposed remotely from window 80 with rotary sector 83 therebetween, detects radiation introduced through window 80, or through rotary sector 83. A converter 85 converts the temperature signal from sensor 84 into an electric signal and applies the electric signal to amplifier 42, which then amplifies same and supplies it as signal $E_T$ to processor 51. Body 75 is of a constant radiation coefficient and is disposed opposite of window 80 with paper 23 therebetween. Also located on the other side of paper 23 opposite to unit 43 is a temperature control system 90 comprising a temperature sensor 87, a control circuit 88, and a heater 89 for keeping body 75 at a predetermined temperature, such as 70° C., for example.

Operation of the microwave sensor of FIG. 7 is as follows. When AGC circuit 74 is energized in timed relation to opening of the gate of sample-and-hold circuit 56, the output signal (reference signal $E_R$) from sample-and-hold circuit 56 is maintained at a constant level. Signal $E_M$ is free from drifts of oscillator 3, detector 8 and other components, so that measuring accuracy is improved. Thus, the arrangement of FIG. 7 requires no arithmetic operations for determining the signal ratio to cancel the drifts. Where the reference signal of the AGC circuit 74 is subjected to a drift of a level which is not negligible, such ratio calculation becomes effective signal processing and results in a more reliable increase in the measuring accuracy.

The constant temperature chamber 81 and hence the rotary sector 83 are controlled by a temperature control circuit which includes control circuit 78, to be kept at a temperature of 50° C. Body 75 is controlled by a temperature control circuit, which includes control circuit 88, to be kept at a temperature of 70° C. During the measurement process, radiation from body 75 is blocked by paper 23 and does not reach window 80. Thus, infrared sensor 84 alternately detects radiation from paper 23 and radiation from rotary sector 83, and temperature detecting system 86 determines a signal $E_T$ indicative of the temperature of paper 23 with the signal from rotary sector 83 being used as a reference signal, and delivers signal $E_T$ to amplifier 42.

Signal processor 51 effects arithmetic operations for effecting temperature compensation and determining, signal $E_t$ (which is the difference between signal $E_t$ and a predetermined temperature) and delivers signals $E_P$ and $E_t$ to display 62.

When a calibration command is generated in the above measurement process (calibration is effected at constant time intervals or as desired), detector head 30 is moved out of the reciprocal scanning zone so that paper 23 can be removed from between window 80 and body 75. As a consequence, infrared sensor 84 alternately detects radiation from body 75 and radiation from rotary sector 83. Temperature detecting system 86 then determines a signal representative of the temperature of body 75, that is, a calibration signal, with the signal from rotary sector 83 is used as a reference signal, and supplies the calibration signal to amplifier 42. The reliability of the temperature signal can be increased and temperature compensation can be performed with accuracy by thus calibrating temperature measuring unit 42 at appropriate times. This will improve the accuracy with which moisture percentages are measured.

Body 75 may be disposed between paper 23 and rotary sector 83 rather than being positioned as shown in FIG. 8, and may be arranged so that it will be placed in the path of measurement radiation, in the vicinity of the window 80, for example, in response to an external signal at the time calibration is to be done.

Figure 10:
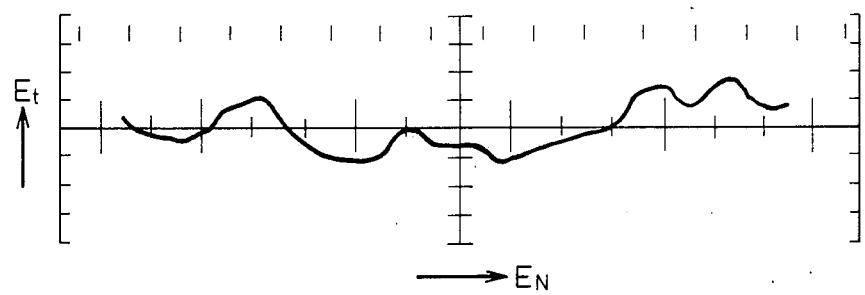
FIG. 10 is a diagram depicting a waveform which is displayed on a display unit of the embodiment of FIG. 7.

Signal $E_t$ generated by signal processor 51 corresponds to variation in the quality (thickness) of paper 23 in the transverse direction thereof for the following reasons. Thus, the displayed waveform (see FIG. 10) which is based on signal $E_t$, serves as effective information in the quality control of paper 23.

In general, paper delivered from a dry part to a calender roll in a paper making plant, is of relatively high temperature and suffers from temperature variations in the transverse direction of the paper. The calender roll is thus heated by the paper and subjected to the same temperature variations in its transverse direction as those of the paper. The portions of the calender roll which have higher temperatures are expanded, while the portions of the calender roll which have lower temperatures are contracted. Thus, the peripheral surface of the calender roll becomes irregular in the transverse configuration thereof.

Therefore, the paper passing through the calender roll suffers from irregular thicknesses in the transverse direction thereof. At this time, thinner portions of the paper have higher temperatures as they correspond to the expanded portions of the calender rolls, while thicker portions of the paper have lower temperatures as they correspond to the contracted portions of the calender rolls. Consequently, the temperature distribution transversely across the paper can be regarded as the distribution of irregular thicknesses in the transverse direction of the paper.

With the arrangement of the invention, the microwave generated by the oscillator 3 is switched between measurement system 44 and reference system 45 by switch 52. The microwaves propagated through the respective systems are detected by the same detector 8 and fed through the sample-and-hold circuits 56,57 to the signal processor 51. The water percentages are determined by using a signal determined by calculating the ratio between measurement and reference signals. This will cancel unwanted influences of drifts of the oscillator, detector and other components, and thus, measuring accuracy is substantially improved.

The AGC circuit (such as shown in FIG. 7) preceding the sample-and-hold circuits and used for keeping the reference signal at a prescribed level also will cause cancellation of unwanted influences due to drifts and thus increases measuring accuracy.

The basis weight and temperature of paper being measured are detected, and basis weight compensation and temperature compensation, are performed on the basis of predetermined temperature compensation characteristics of moisture percentage parameters and gauge reading versus basis weight characteristics of the moisture percentage parameters, so that undesirable influences due to variations in basis weight and temperature of the paper can be compensated for to thereby increase the measuring accuracy.

The foregoing description is illustrative of the principles of the invention. Numerous modifications and extensions thereof would be apparent to the worker skilled in the art. All such modifications and extensions are to be considered to be within the spirit and scope of the invention.

What is claimed:

1. A microwave moisture sensor for sensing moisture percentages in a travelling sheet like material at selected location thereof transverse to the direction of travel without any physical contact between the sensor and the sheet like material, said sensor comprising
    a microwave oscillator;
    a first microwave transmitting horn antenna for radiating a microwave generated by said oscillator to said sheet like material;
    a first microwave receiving horn antenna for receiving said microwave transmitted by said first transmitting horn antenna and radiated through said sheet like material;
    a second microwave transmitting horn antenna connected to said first microwave receiving horn antenna for re-radiating said microwave to said sheet like material;
    a second microwave receiving horn antenna for receiving said microwave transmitted by said second transmitting horn antenna and radiated through said sheet like material;
    wherein said first transmitting horn antenna and said second receiving horn antenna are located on one side of said sheet like material, and said second transmitting horn antenna and said first receiving horn antenna are located on another side of said sheet like material;

a measurement system comprising said first and second transmitting horn antennas and said first and second receiving horn antennas
a reference system comprising a microwave propagation path excluding said measurement system;
switching means, interconnecting said microwave oscillator to said measurement system and to said reference system, for switching said microwave generated by said oscillator to be applied selectively to said measurement system and to said reference system;
a single detector for detecting signals from said reference system and signals from said measurement system and for producing a measurement signal having varying amplitudes as measured and representing said signal from said measurement system, and for producing a reference signal having a constant amplitude and representing said signal from said reference system;
guide means, connected to said switching means, for guiding to said single detector, without interference, said signal from said measurement system and said signal from said reference system;
basis weight detecting means for detecting the basis weight of said sheet like material, said basis weight detecting means comprising a radiation source disposed on one side of said sheet like material, an ionization chamber disposed on the other side of said sheet, and amplifier means connected to said ionization chamber for producing a basis weight signal;
temperature detecting means for detecting the temperature of said sheet like material and for producing a signal indicative of said temperature;
sampling means, comprising a pair of sample and hold circuits, for separately sampling said measurement signal and said reference signal, respectively, from said single detector and from said guide means, concurrently with the switching of said switching means, and for separately holding the sampled measurement signal and reference signal for processing by a signal processing means;
a control unit for selectively controlling said switching means and said sample and hold circuits so that the measurement signal and reference signal are generated and sampled and held; and
said signal processing means, connected to said temperature detecting means, to said amplifier means for said basis weight detector means, and to said sampling means, for determining the moisture percentage at selected locations of said sheet like material, said signal processing means comprising a computer connected to a random access memory and to a read only memory, wherein said signal processing means comprises logic for calculating the ratio of said measurement signal to said reference signal using said sampled measurement signal having variable amplitudes, and said sampled reference signal having constant amplitudes, to obtain measured water content;

initializing said temperature signal to determine surface temperature of said sheet like material;

compensating said surface temperature using a characteristic curve defining temperature coefficient versus temperature of said sheet like material to obtain compensated surface temperature;

calculating moisture percentage using said measured water content, said compensated surface temperature, said basis weight signal and a characteristic curve defining water content versus basis weight of said sheet like material to obtain a signal indicative of said moisture percentage; and outputting said signal indicative of said moisture percentage;

wherein said moisture percentage is substantially free of effects of drift in components of said sensor.

2. The sensor of claim 1, wherein said sampling means comprises an automatic gain circuit for keeping said reference signal at a prescribed level.

3. The sensor of claim 1, wherein said temperature detecting means comprises a radiation emitting device for emitting radiation to said sheet of material; means for detecting said radiation on said sheet like material; means for periodically interrupting the radiation from said sheet like material to said means for detecting, means for detecting a reference radiation applied during the time the means for periodically interrupting interrupts the radiation from the sheet like material; and means for calibrating said temperature detecting means comprising means for moving said sheet like material out of scanning range of said detecting means and means for equalizing the temperature of said radiation emitting device and the temperature of the space close to said means for periodically interrupting.

* * * * *